US008563934B2

(12) United States Patent
Yao et al.

(10) Patent No.: US 8,563,934 B2
(45) Date of Patent: Oct. 22, 2013

(54) METHOD AND DETECTION SYSTEM FOR DETECTION OF AFLATOXIN IN CORN WITH FLUORESCENCE SPECTRA

(75) Inventors: Haibo Yao, Slidell, LA (US); Zuzana Hruska, Covington, LA (US); Russell D. Kincaid, New Orleans, LA (US); Thomas E. Cleveland, Mandeville, LA (US); Robert L. Brown, Prairieville, LA (US)

(73) Assignee: Mississippi State University, Mississippi State, MS (US)

( * ) Notice: Subject to any disclaimer, the term of this patent is extended or adjusted under 35 U.S.C. 154(b) by 601 days.

(21) Appl. No.: 12/807,673

(22) Filed: Sep. 10, 2010

(65) Prior Publication Data

US 2012/0061586 A1    Mar. 15, 2012

(51) Int. Cl.
G01J 1/58    (2006.01)

(52) U.S. Cl.
USPC .............. 250/339.12; 250/339.11; 250/338.1; 250/341.8; 250/339.1; 250/459.1

(58) Field of Classification Search
USPC .................................................... 250/339.12
See application file for complete search history.

(56) References Cited

U.S. PATENT DOCUMENTS

| | | | |
|---|---|---|---|
| 4,181,853 A * | 1/1980 | Abu-Shumays et al. ..... | 250/304 |
| 4,285,698 A * | 8/1981 | Otto et al. ....................... | 436/20 |
| 4,535,248 A * | 8/1985 | Schade et al. .............. | 250/459.1 |
| 4,622,469 A | 11/1986 | Akiyama | |
| 4,795,651 A | 1/1989 | Henderson et al. | |
| 4,818,687 A | 4/1989 | Groopman et al. | |
| 4,866,283 A * | 9/1989 | Hill, Jr. ...................... | 250/461.2 |
| 5,539,517 A * | 7/1996 | Cabib et al. ................... | 356/456 |
| 5,689,333 A * | 11/1997 | Batchelder et al. .......... | 356/301 |
| 5,790,188 A * | 8/1998 | Sun ............... | 348/144 |
| 5,866,430 A * | 2/1999 | Grow ................. | 506/6 |
| 5,914,247 A | 6/1999 | Casey et al. | |
| 6,002,476 A * | 12/1999 | Treado .......................... | 356/301 |
| 6,211,906 B1 * | 4/2001 | Sun ............................ | 348/144 |
| 6,495,818 B1 | 12/2002 | Mao | |
| 6,512,236 B2 | 1/2003 | Seville | |
| 6,734,962 B2 * | 5/2004 | Treado et al. ................. | 356/301 |
| 6,786,221 B2 * | 9/2004 | Lane ............................. | 131/309 |

(Continued)

OTHER PUBLICATIONS

Barbini et al., Laser Remote Monitoring of the Plant Photosynthetic Activity, Proc. SPIE, 1995, pp. 57-65, vol. 2585, USA.

(Continued)

Primary Examiner — David Porta
Assistant Examiner — Djura Malevic
(74) Attorney, Agent, or Firm — Kristin L. McCandless

(57) ABSTRACT

A system and method for fluorescence spectral imaging of target material to detect the presence of a contaminant (such as aflatoxin in corn) is provided. An ultraviolet light source is coupled with a light-excluding compartment. The fluorescence from the UV excited target passes through a filter (liquid crystal tunable, acoustic-optic tunable, a filter wheel, or other wavelength splitting device) and a lens, to a spectral imaging camera. Fluorescence spectral image data from the camera are analyzed by a computer and presented in human-readable form. Aflatoxin detection in contaminated corn kernels is based on peak fluorescence and peak fluorescence shift in the spectral range from 451 nm to 500 nm. Aflatoxin contamination level within the target material is quantified based on peak fluorescence and peak fluorescence shift and computed corn kernel pixel statistics.

27 Claims, 5 Drawing Sheets

(56) References Cited

U.S. PATENT DOCUMENTS

Figure 1:
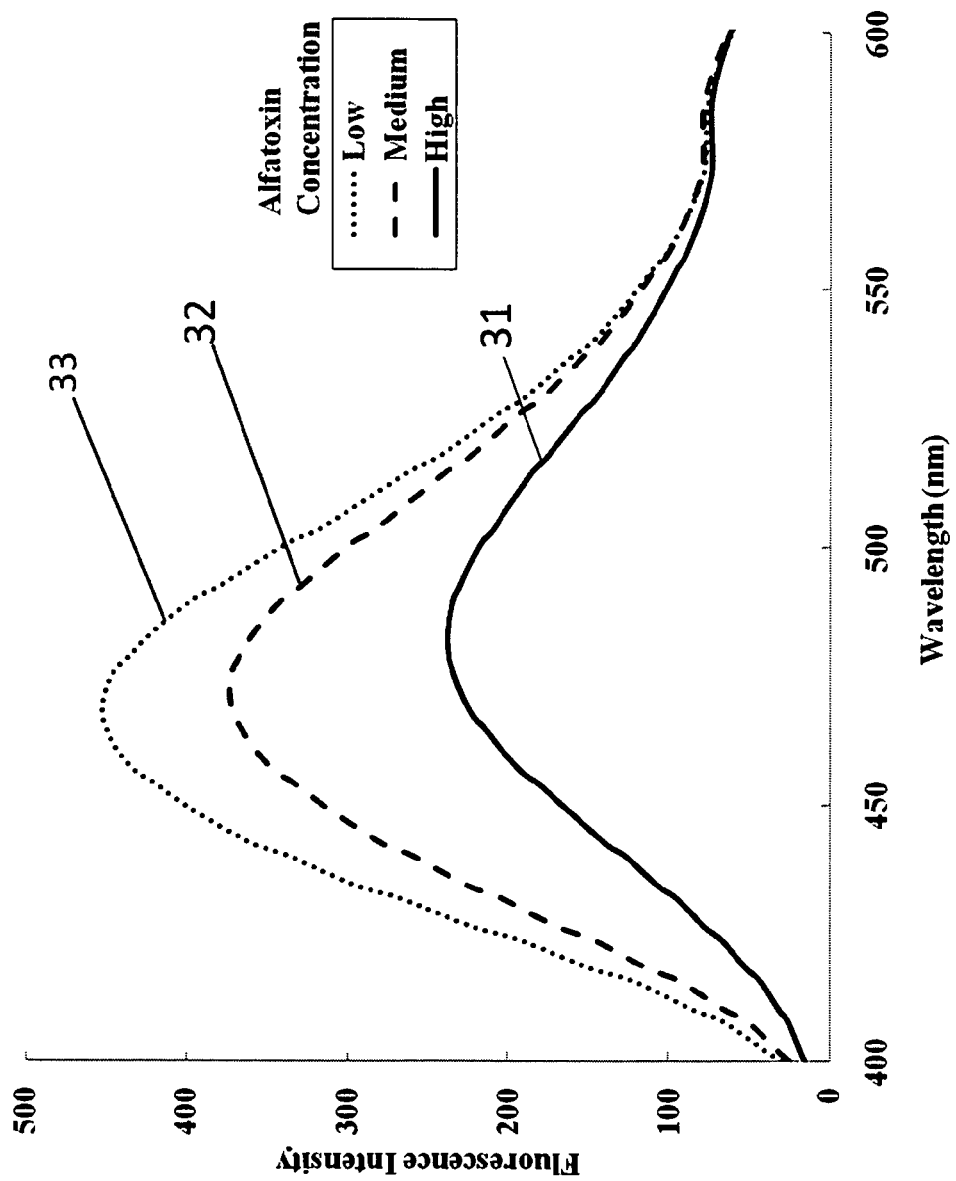

| | | | | |
|---|---|---|---|---|
| 7,532,320 | B2* | 5/2009 | Neiss et al. | 356/301 |
| 7,755,756 | B2* | 7/2010 | Stewart et al. | 356/301 |
| 8,344,334 | B2* | 1/2013 | Coker et al. | 250/459.1 |
| 8,384,046 | B2* | 2/2013 | Haidekker et al. | 250/459.1 |
| 8,395,769 | B2* | 3/2013 | Stewart et al. | 356/301 |
| 8,406,859 | B2* | 3/2013 | Zuzak et al. | 600/476 |
| 2003/0025086 | A1* | 2/2003 | Stroka | 250/461.1 |
| 2005/0185178 | A1* | 8/2005 | Gardner et al. | 356/301 |
| 2007/0024946 | A1* | 2/2007 | Panasyuk et al. | 359/253 |
| 2008/0192246 | A1* | 8/2008 | Neiss et al. | 356/301 |
| 2010/0056928 | A1* | 3/2010 | Zuzak et al. | 600/476 |
| 2011/0007309 | A1* | 1/2011 | Stewart et al. | 356/301 |

OTHER PUBLICATIONS

Yao et al., Hyperspectral Bright Greenish-Yellow Fluorescence (BGYF) Imaging of Aflatoxin Contaminated Corn Kernels, Proc. SPIE, Optics for Natural Resources, Agriculture, and Foods, 2006, USA.

Ononye et al., Automatic Detection of Aflatoxin Contaminated Corn Kernels Using Dual-Band Imagery, Proc. SPIE, 2009, vol. 7315, 73150R, USA.

Kim et al., Hyperspectral Reflectance and Fluorescence Imaging System for Food Quality and Safety, 2001 American Society of Agricultural Engineers, pp. 721-729, vol. 44(3).

Yao et al., Differentiation of Toxigenic Fungi Using Hyperspectral Imagery, Sens. & Instrumen. Food Qual., 2008, 2:215-224, USA.

Yao et al., Classification of Aflatoxin Contaminated Corn Kernels Using Fluorescence Hyperspectral Imaging Data, presented to ISM Conference, Sep. 11, 2009.

Yao et al., Correlation and Classification of Single Kernel Fluorescence Hyperspectral Data with Aflatoxin Concentration in Corn Kernels Inoculated with Aspergillus flavus Spores, Food Additives and Contaminants, May 2010, pp. 701-709, vol. 27, No. 5.

* cited by examiner

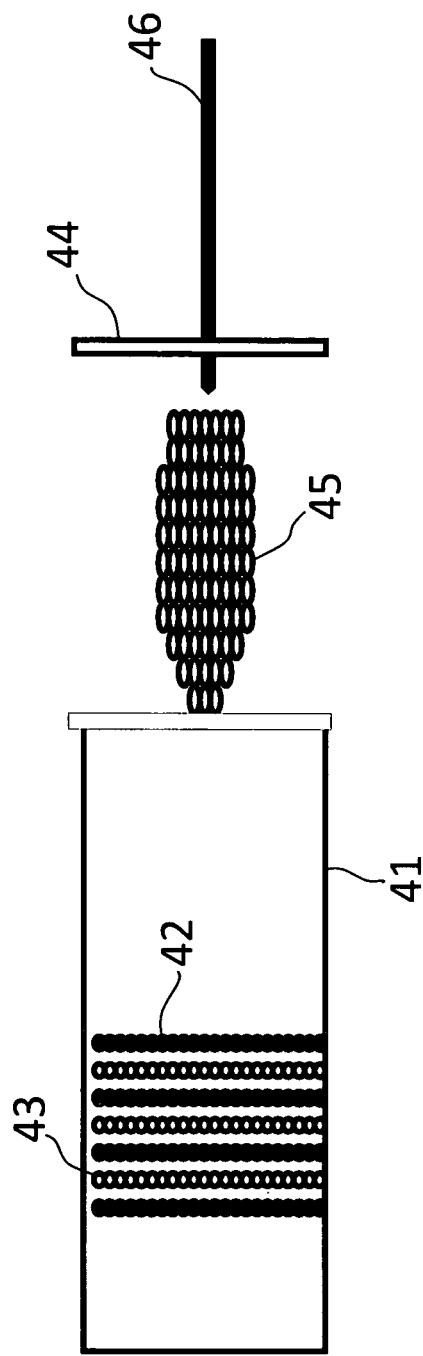
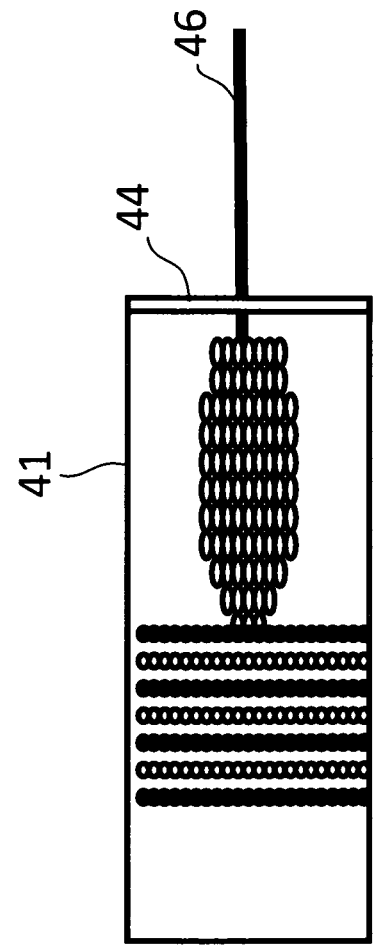
FIG. 5a
FIG. 5b

METHOD AND DETECTION SYSTEM FOR DETECTION OF AFLATOXIN IN CORN WITH FLUORESCENCE SPECTRA

This invention was made with Government support under 58-6435-9-425 awarded by the U.S. Department of Agriculture, Agriculture Research Service. The Government may have certain rights in the invention.

BACKGROUND AND SUMMARY OF THE INVENTION

The present invention generally relates to methods utilizing optical systems for the detection of mycotoxins in grain. More specifically, the invention is directed to the detection of the mycotoxin aflatoxin in pre and post-harvest corn samples. Furthermore, the invention can also be deployed in the field where, due to various environmental changes, aflatoxin contamination naturally occurs.

Aflatoxins are toxic secondary metabolites produced by fungi of the genus *Aspergillus* under stressed conditions. Aflatoxin producing members of *Aspergillus* are common and widespread in nature. They can colonize and contaminate grain before harvest or during storage. Host crops are particularly susceptible to infection by *Aspergillus* and consequent aflatoxin contamination, following prolonged exposure to a high humidity environment or damage from stressful conditions such as drought. Aflatoxins have received greater attention than any other mycotoxins because of their demonstrated potent carcinogenic effect in susceptible laboratory animals and their acute toxicological effects in humans. Because absolute safety can never be realistically achieved, many countries have attempted to control exposure to aflatoxins by imposing regulatory limits on commodities intended for use as food and feed.

Sampling and sample preparation remain a considerable source of error in the analytical identification of aflatoxins. Thus, systematic approaches to sampling, sample preparation, and analysis are absolutely necessary to determine aflatoxins at the parts-per-billion level. A common feature of all sampling plans is that the entire primary sample must be ground and mixed so that the analytical test portion has the same concentration of toxin as the original sample. The unfortunate result of this type of aflatoxin determination is the destruction of the original sample.

All analytical procedures include three steps: extraction, purification, and determination. Solid-phase extraction is used to clean up test extracts before instrumental analysis (for example, thin layer or liquid chromatography) to remove co-extracted materials that may interfere with the determination of target analytes.

Thin layer chromatography (TLC), also known as flat bed chromatography or planar chromatography, is one of the most widely used separation techniques in aflatoxin analysis. Thin layer chromatography has been considered the official method and the method of choice of the Association of Official Analytical Chemists (AOAC) to identify and quantify aflatoxins at levels as low as 1 ng/g. The method is also used to verify findings by newer, more rapid techniques.

Liquid chromatography (LC) is similar to TLC in many respects, including analyte application, stationary phase, and mobile phase. Liquid chromatography and TLC complement each other. It is quite common for an analyst to use TLC for preliminary work to optimize LC separation conditions. Liquid chromatography methods for the determination of aflatoxins in foods include normal-phase LC (NPLC), reversed-phase LC (RPLC) with pre- or before-column derivatization (BCD), RPLC followed by postcolumn derivatization (PCD), and RPLC with electrochemical detection.

Thin layer chromatography and LC methods for determining aflatoxins in food are laborious and time consuming. Often, these techniques require knowledge and experience of chromatographic techniques to solve separation and interference problems. Through advances in biotechnology, highly specific antibody-based tests are now commercially available that can identify and measure aflatoxins in food in less than 10 minutes. These tests are based on the affinities of the monoclonal or polyclonal antibodies for aflatoxins. The three types of immunochemical methods are radioimmunoassay (RIA), enzyme-linked immunosorbent assay (ELISA), and immunoaffinity column assay (ICA) similar to U.S. Pat. No. 4,818,687.

Safety is a key issue for scientists working in the aflatoxin area. Steps must be taken to minimize exposure to the toxins as well as to the producing microorganisms, *Aspergillus flavus* and *Aspergillus parasiticus*. A safety program should be established that meets the requirements of the Laboratory Standard of the Occupational Safety and Health Administration (1990) and the guidelines of the National Institutes of Health (1981) covering use of chemical carcinogens.

A non-invasive method for separating aflatoxin-contaminated from non-contaminated grains, kernels, seeds and nuts was disclosed in U.S. Pat. No. 4,795,651 to Henderson, et al., in 1989. The process involved using dynamic flotation to separate contaminated and uncontaminated substances based on specific gravity because aflatoxin contaminated commodities appear to have lower specific gravity than uncontaminated ones. Although quite reliable, the process is lengthy and not practical for processing large quantities of grain as it requires wetting and re-drying individual grains including corn kernels.

U.S. Pat. No. 4,535,248 discloses an approach for non-invasive rapid detection of aflatoxin. This patent utilizes long wave ultraviolet radiation for detecting aflatoxin contamination in almonds. The method detects the presence of aflatoxin based on evidence of violet-purple fluorescence. A similar method utilizing bright greenish-yellow (BGY) fluorescence was employed for detecting possible aflatoxin contamination in corn kernels. The reasoning behind using the method was based on the premise that seed contaminated with *A. flavus* is often associated with BGY fluorescence. However, the presence of BGY fluorescence may or may not indicate aflatoxin contamination in corn kernels, and thus introduces high false positive errors in detection. Therefore, the method is no longer used in corn as an aflatoxin detection method, but only a screening method for kernels requiring further investigation.

Hyperspectral imaging systems have been used for a diverse range of remote sensing and other analytical techniques, such as is disclosed, for example, in U.S. Pat. No. 5,790,188 and the related U.S. Pat. No. 6,211,906. Hyperspectral imaging has also been used in conjunction with microscopic optical systems, such as disclosed, for example, in U.S. Pat. No. 6,495,818. In such systems, radiation reflected by or emanating from a target or specimen is detected in a large number of narrow contiguous spectral bands, producing a data set which is distributed not only spatially, but spectrally as well. That is, for each pixel within an image of the target, information is recorded in each of the spectral bands, thereby producing a three-dimensional hyperspectral image cube, in which spectral information for each pixel is distributed across a spectral axis perpendicular to the spatial axes.

Narrow band spectral reflectance across a wide spectral range (for example, UV, visible near-infrared, and short wave near-infrared) can provide rich spectral signature information regarding suspicious targets. The spectral signature can then be used for separation of specific targets such as aflatoxin contaminated and non-contaminated corn. The process involves irradiating corn kernels with magnetic radiation (such as a light source working under a certain wavelength range), measuring reflected radiation from the kernels with electronic devices (such as a CCD array that is sensitive in a certain wavelength range), composing a target signature from the captured signals, and implementing detection/separation algorithms for detecting aflatoxin in corn. The present invention applies this spectral based approach along with a UV light source and uses spectral fluorescence information for aflatoxin detection.

Similar systems that use spectral information for various applications have been described in the past. Most such systems utilize a technique in which the suspicious item is irradiated with light having a frequency (for example, UV, visible near-infrared, and short wave near-infrared) such that it causes the emission of fluorescent radiation upon striking the target. The fluorescent light from the target is then measured and compared with a threshold value. If the light thus gathered exceeds the threshold, the detection algorithm can generate a signal indicating the presence of the target. Such a system is disclosed, for example in U.S. Pat. No. 4,622,469 to Akiyama for detecting rotten albumen in broken raw eggs, U.S. Pat. No. 6,512,236 B2 to Seville for viewing patterns of fluorescently stained DNA, protein or other biological materials, and U.S. Pat. No. 5,914,247 to Casey et al., for a fecal and ingesta contamination detection system based on the premise that the emission of fluorescence between 660 and 680 nm is indicative of the presence of ingesta or fecal matter.

Radiation-induced fluorescence has also been applied in vegetation remote sensing studies. For example, it has been shown that there is a shift in the fluorescence signature of a stressed plant compared to a healthy plant (Barbini, et al., Laser Remote Monitoring of the Plant Photosynthetic Activity, SPIE, Vol. 2585, (1995), pp. 57-65).

Fluorescence hyperspectral images were collected with an aggregation of corn kernels (Yao et al., Hyperspectral Bright Greenish-Yellow Fluorescence (BGYF) Imaging of Aflatoxin Contaminated Corn Kernels, Proc. of SPIE, Optics for Natural Resources, Agriculture, and Foods, 2006). The study reported that the aggregated bright greenish-yellow (BGY) fluorescence corn kernels had fluorescence peaks at around 500 nm and 514 nm. It was later determined that the imaging system was not properly calibrated for wavelength thus the reported fluorescence spectra were not correct. The experiment used 365 nm UV-LED as excitation light source. However, in this initial exploratory study, no excitation and emission filters were used. The recorded spectra were mixed with signal from the light source. As a consequence, the resulted spectra were not representative to aflatoxin contaminated corn kernels. Lastly, the study used only one group of BGY fluorescence corn kernels for imaging. In order to document the relationship between fluorescence spectra and aflatoxin contamination, single kernel imaging and chemical analysis is needed. Consequently, no conclusion could be drawn based on this study.

Two-band fluorescence image data at 450 nm and 505 nm were used for aflatoxin detection in corn kernels (Ononye et al., Automatic Detection of Aflatoxin Contaminated Corn Kernels Using Dual-Band Imagery, Proc. of SPIE, Vol. 7315, 73150R, 2009). The corn sample size was 25 g. The samples were excited with 365 nm UV light source and image data were collected with a Nuance Multispectral Imaging System (Cambridge Research Institute, MA). The imaging system was equipped with a built-in liquid crystal tunable filter that was tuned to 450 nm and 505 nm. Since the study used 25 g of corn kernels as one sample, the relationship between fluorescence spectra and aflatoxin contamination in single corn kernel could not be established. This study did not produce a plot of the fluorescence spectra. Thus, characteristics of the fluorescence spectra, such as fluorescence peak and shift could not be determined in the study.

The present invention provides techniques and devices for detection of aflatoxin in corn by fluorescence spectral imaging. The fluorescence spectral image is a three dimensional "image" where one dimension contains spectral information and the other two dimensions contain spatial information. The spectral data of the image can be analyzed on a pixel-by-pixel basis for the mycotoxin in question and its spatial extent. Thus, the techniques are non-invasive and do not require introduction of agents typically required to facilitate interaction with illumination sources. The techniques also have minimal requirements in sample preparation and can generate identification results in a short period of time once the image is acquired.

An objective of the present invention is to use spectral information of the mycotoxin aflatoxin in order to detect it in a target material, such as in corn samples. The invention may be embodied in the form of, for example, tabletop lab equipment or a portable system to be used at specific inspection sites. Our research has discovered that a single aflatoxin-contaminated corn kernel has distinct spectral fluorescence features. Our research further shows that these spectral fluorescence features can be used for aflatoxin contamination detection and quantification. The invention thus incorporates technical details and possible embodiments for aflatoxin detection in corn using spectral fluorescence. This invention in real time will allow the user to collect an infinite number of images and requires no knowledge of aflatoxin chemistry.

Another objective of the present invention is to provide for implementation of fluorescence excitation sources, data capture devices, database of reference fluorescence spectra, processing methods, and identification algorithms.

A further objective of this invention is to provide a method for processing the fluorescence spectra emitted from corn kernels, a method which also produces a signal that reliably indicates aflatoxin contamination, and apparatus which implement such method.

Another objective of this invention is to differentiate between healthy and aflatoxin contaminated corn based on fluorescence emission under direct long wavelength ultraviolet excitation, and utilize peak fluorescence and peak fluorescence shift for aflatoxin detection in corn.

Another objective is to provide details of a tabletop system, which is a possible embodiment of this invention that can be used in lab environments such as analytical labs, for aflatoxin detection in corn. The tabletop system is for detecting contamination in larger corn samples (approximately 25-1000 g). Such a system includes an operation computer, fluorescence excitation source with a specific wavelength centered around 365 nm, image capture devices, database of reference fluorescence spectra, processing methods, and identification algorithms.

An additional objective is to provide details of a portable system which can be used at various inspection sites such as grain inspection stations, silos, or in the field for aflatoxin detection in corn. The portable system is for detecting contamination in smaller corn samples (approximately from a single corn kernel to an entire corn ear). Such a system includes an embedded operation computer, fluorescence excitation source with a specific wavelength centered around 365 nm, spectral data capture devices, database of reference fluorescence spectra, processing methods, and identification algorithms.

A further objective is to incorporate a fluorescence excitation source in the detection system. Such excitation source can consist of a UV fluorescence lamp or a UV LED that radiates at long ultraviolet wavelengths and an excitation filter centered at 365 nm.

An additional objective of this invention is to provide a non-invasive aflatoxin detection system that can quickly and accurately detect and quantify aflatoxin contamination in corn.

The invention includes an imaging camera, micro-spectrometer array, or photodiode detector array for fluorescence spectral data acquisition, a fluorescence excitation source, digital reference library of pertinent fluorescence spectra, and the appropriate identification algorithm/software. The identification process is completely non-invasive, and rapid for real time work. The procedure can be automated, and its determination is objective because no human judgment is involved.

Other objects, advantages and novel features of the present invention will become apparent from the following detailed description of the invention when considered in conjunction with the accompanying drawings.

BRIEF DESCRIPTION OF THE DRAWINGS

FIG. 1 is a graph of observed fluorescence intensity with 365 nm ultraviolet excitation as a function of aflatoxin concentration in single corn kernels and incident radiation wavelength.

FIG. 2 is a schematic perspective view of a tabletop fluorescence spectral imaging system in accordance with an embodiment of the present invention.

FIG. 3 is a flow chart of a method of fluorescence spectral imaging in accordance with an automated tabletop system embodiment of the present invention.

FIG. 4 is a flow chart of the image processing method of a method of fluorescence spectral imaging in accordance with an embodiment of the present invention.

FIG. **5*a*** is a top view of a portable fluorescence spectral imaging system with the target material not inserted into the imaging compartment in accordance with an alternative embodiment of the present invention.

FIG. **5*b*** is a top view of a portable fluorescence spectral imaging system with the target material inserted into the imaging compartment in accordance with an alternative embodiment of the present invention.

DETAILED DESCRIPTION OF THE DRAWINGS

FIG. 1 illustrates a typical spectrum of detected luminescence observed from UV excitation of single corn kernels as a function of the aflatoxin concentration present in the single corn kernel samples. At high aflatoxin concentrations, illustrated by line 31, the peak value of the emitted spectrum is lower than the peak values of corn containing medium and low aflatoxin concentrations (lines 32 and 33, respectively). In addition, as the aflatoxin concentration increases, the wavelength of the detected spectrum at the peak intensity value shifts toward a higher wavelength. Both the decrease in peak value and the shift of wavelength at the peak value are factors that may be taken into account in the determination of the extent of aflatoxin concentration present in the target material. As shown, the peak fluorescence and peak fluorescence shift features are in the spectral range from 451 nm to 500 nm.

FIG. 2 shows an embodiment of the present invention intended for "table top" or production imaging environments. In this embodiment, a compartment 11 is provided with a platform 12, preferably a conveyor, for passing target material 13, preferably corn, through a fluorescence spectral imaging field. The size of the compartment 11 is not limited to laboratory-sized environments, but may be large enough to permit continuous scanning of corn passing through an agricultural or industrial production facility in large quantity. Alternatively, a target material sample stream may be diverted from a production stream, and fed to platform 12 to maintain high production flow rates while ensuring appropriate representative sampling of the target material is performed. Platform 12 may also include a tray, or some other suitable means for placing the target material into the spectral imaging field within the compartment 11.

UV excitation of the spectral imaging field in the tabletop environment is preferably provided by two UV light sources 14 with embedded excitation filters 15 to illuminate platform 12. Both the UV light sources 14 and the excitation filters 15 are centered at 365 nm. The fluorescence spectral imaging assembly includes wavelength splitting optical instrument 16, preferably a liquid crystal tunable filter, focusing device 17, preferably a lens, spectral data acquisition device 18, preferably an imaging camera, and front-mounted long pass emission filter 19. Under appropriate circumstances, spectral data acquisition device 18 may also be a photodiode detector array or with appropriate modifications, a micro-spectrometer. Emission filter 19 is preferably front-mounted and blocks transmission of ultraviolet light with wavelength less than 400 nm from entering wavelength splitting optical instrument 16. The spectral imaging assembly is mounted over aperture 20 to receive excited luminescence from the target material. In order to optimize fluorescence spectral imaging, compartment 11 is arranged such that it contains the UV light and excludes outside light. The distance between aperture 20 and target material 13 is considered the imaging distance. During data acquisition there is a certain imaging distance and a certain duration of imaging for data acquisition optimization. The optimized imaging distance and imaging duration is determined by the setup of the fluorescence spectral imaging system. The fluorescence spectral imaging data recorded by spectral data acquisition device 18 is transferred to a computer analysis system (not shown in FIG. 2) for data analysis and generation of human-readable imaging information display.

The wavelength splitting optical instrument 16, preferably a liquid crystal tunable filter, is to tune the excited fluorescence spectra into specific key wavelengths during fluorescence spectral imaging acquisition. The tunable feature of the spectral imaging system can also be achieved using other wavelength selection devices such as an acoustic-optic tunable filter or a filter wheel with a set of predefined filters. This tunable feature enables the imaging system to do rapid data acquisition over the key wavelengths which in turn makes rapid aflatoxin detection possible after real time image analysis. Alternatively, a spectrograph or set of separate filters having predefined wavelengths may also be used for wavelength splitting optical instrument 16. In this embodiment of the invention, the specific key wavelengths are from 451 nm to 500 nm in order to capture the peak fluorescence and peak fluorescence shift phenomenon exhibited by aflatoxin contaminated corn. The number of defined image bands in this wavelength range can be varied, as long as the peak fluorescence and peak fluorescence shift phenomenon is determined in the image. The peak fluorescence and peak fluorescence shift phenomenon and other spectral features are then used for aflatoxin contamination detection and quantification in corn. Aflatoxin contamination detection and quantification are discussed in more detail in the detailed descriptions for FIG. 3 and FIG. 4.

Figure 3:
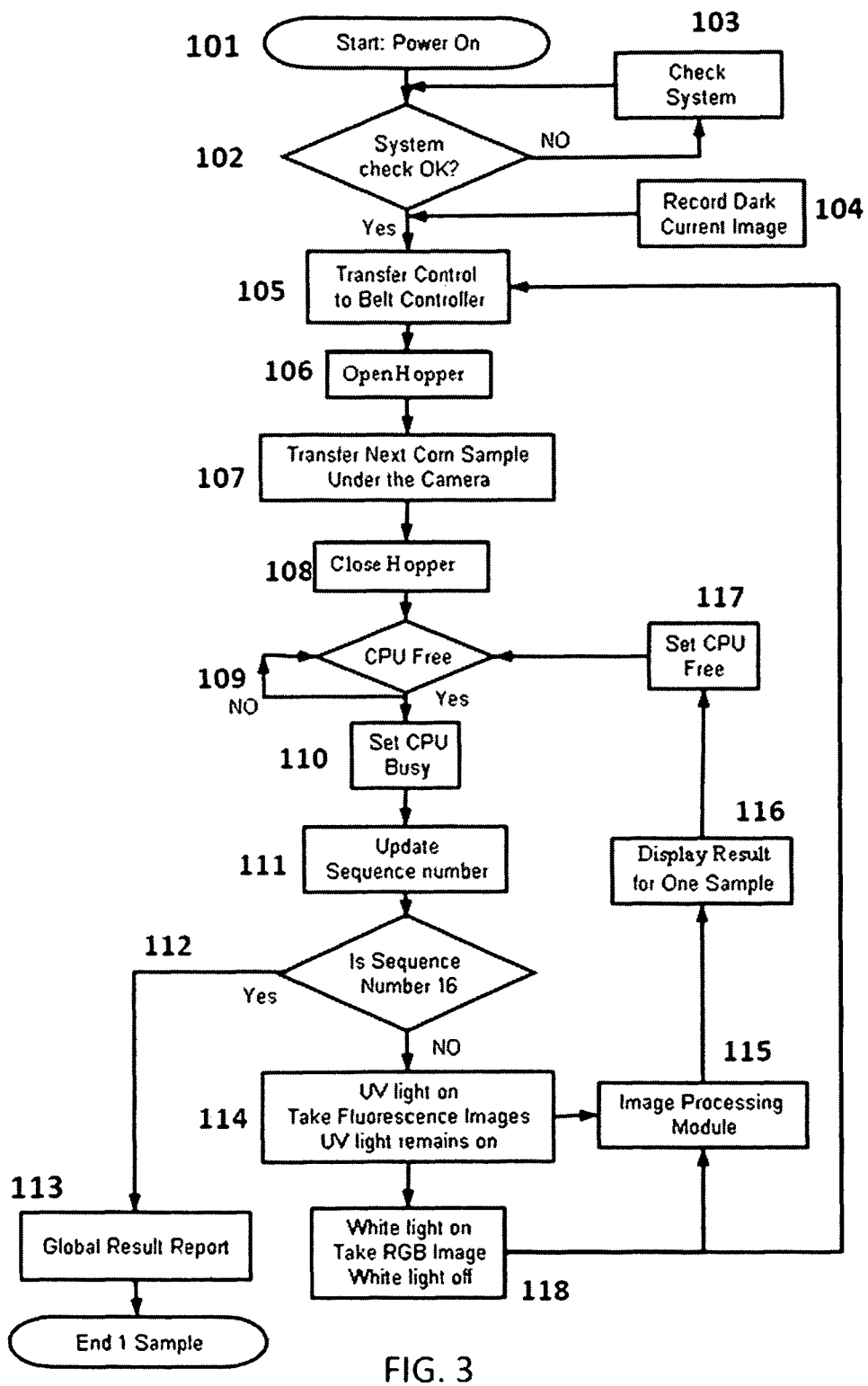

An embodiment of a method for fluorescence spectral imaging in accordance with the present invention is detailed in the flow chart provided in FIG. 3. Upon powering up the fluorescence spectral imaging system at step 101, a system check is performed at step 102. If the system check is not completed successfully, additional system checks are performed in step 103. Following successful completion of the system check, the spectral data acquisition device records a current dark image without the presence of target material and UV light for calibration purposes in step 104.

After the completion of these system initiation steps, the fluorescence spectral imaging system computer in step 105 transfers control to a conveyor belt controller to begin the feed of target material into the spectral data acquisition device's field of view. Upon activation of the conveyor, a target material feed hopper is controlled to open in step 106 to begin feeding the target material (in this embodiment, corn) to the imaging compartment in step 107. If desired for target material flow control, the feed hopper may be closed at step 108 during the fluorescence spectral imaging of the conveyed target material.

The central processing unit (CPU) of the computer analysis system is checked at step 109 to determine whether the CPU is free. If the CPU is free, in step 110 a flag is set to indicate that the CPU is busy, and the process proceeds to step 111. In step 111, the sequence number for the current iteration of a multiple-exposure sequence of fluorescence spectral imaging is updated to the next sequence number. Next, at step 112, a check is made to determine whether the maximum sequence number, i.e., the last of the iterations of the multiple-exposure sequence has been reached. The total number of sequence iterations is defined by corn sample size. For example, it takes 16 images to finish 1 kg of corn, thus giving a total sequence number of 16. If the maximum sequence number has been reached, the process shifts to step 113 to generate a global result report for human review, and ends the fluorescence spectral imaging process.

Figure 2:
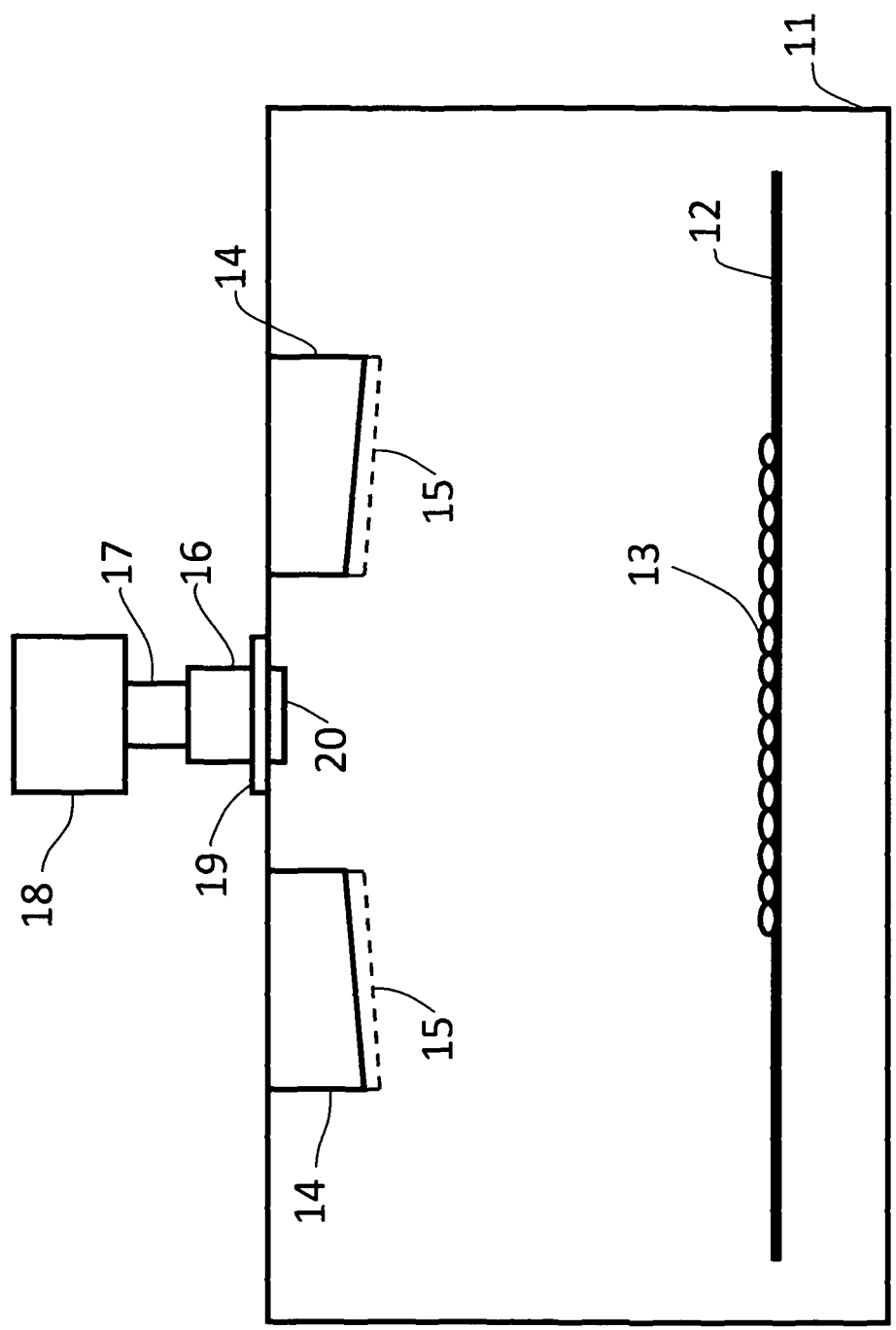

If the sequence number has not reached the maximum number, then in step 114 the UV light source(s) 14, as shown in FIG. 2, provides UV light to the target material (corn) 13, shown in FIG. 2, while fluorescence spectral images are obtained by the spectral data acquisition device and transferred to the computer analysis system's image processing module in step 115. More details of step 115 are provided in the detailed description of FIG. 4. Following processing, a sample of the fluorescence imaging result is displayed in step 116, and then an instruction to set the CPU flag to "free" is issued in step 117.

In the meantime while the image processing, display and CPU flag reset is being executed, the UV light source(s) 14, as shown in FIG. 2, remains on, and in step 118 a white light is turned on to permit the capture of a visible light image (a "RGB" or red, green, blue image) of the target material. The image is also passed to the image processing module for processing and display as in steps 115 and 116. After the last iteration of the sequence, control of the process loops from step 118 back to step 105, thereby permitting the imaging process to begin anew on the next batch of target material.

Figure 4:
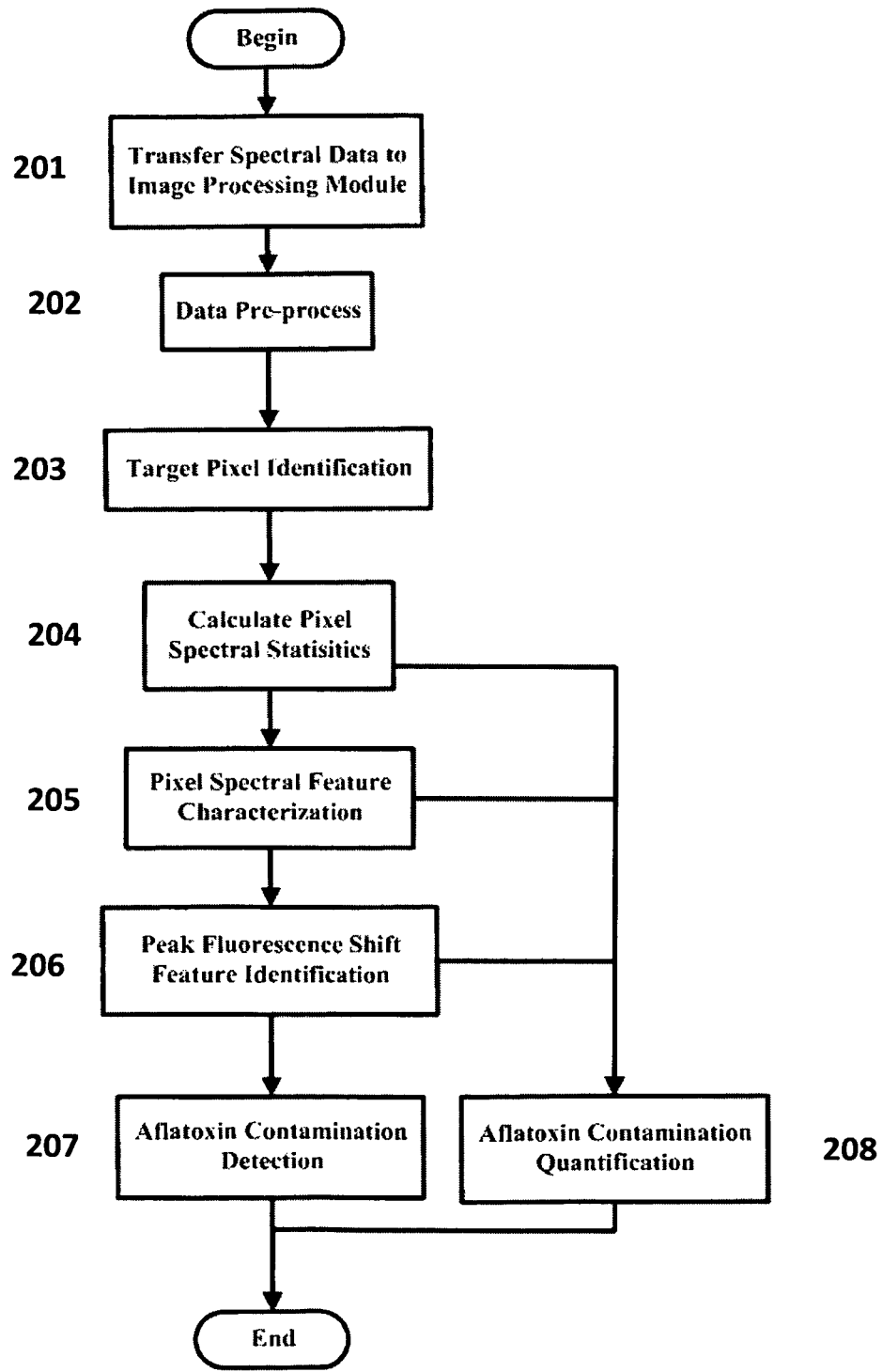

An embodiment of the computer analysis system's processing of the fluorescence spectral image data from the fluorescence images in step 115, as shown in FIG. 3, is further detailed in the flow chart provided in FIG. 4. In this embodiment, the fluorescence spectral data are passed from the spectral data acquisition device to the image processing module in step 201. The fluorescence spectral data are then pre-processed in step 202, including dark current removal, image calibration to convert from radiance values received at the sensor to fluorescence values of the target materials, spectral noise smoothing and noisy band removal. In step 203 image pixels associated with the target material (in this embodiment the target material is corn) in the fluorescence spectral images are identified.

Step 204 computes statistics of spectral features for each corn pixel, the spectral features being fluorescence spectrum values for each corn pixel representing fluorescence intensity, mean, median, standard deviation, skewness and kurtosis. Step 205 characterizes fluorescence spectral features of each corn pixel, the fluorescence spectral features of each corn pixel extracted from the spectral image being in the spectral range from 451 to 500 nm, where the features being characterized include first order derivative, second order derivative when applicable, peak fluorescence location, and peak fluorescence value. In addition, normalized peak fluorescence difference index (NPFDI) may be calculated using peak fluorescence value extracted from 451 to 500 nm and fluorescence value from a spectral band with shorter wavelength. In order to maximize the calculated difference in NPFDI, the shorter wavelength may be selected as 400 nm (emission filter 19, as shown in FIG. 2). Thus, NPFDI may be calculated as (peak fluorescence value−fluorescence value at 400 nm)/(peak fluorescence value+fluorescence value at 400 nm). Step 206 identifies peak fluorescence and peak fluorescence shift features within the characterized fluorescence spectral features, the peak fluorescence and peak fluorescence shift features being an indication of changes in the respective fluorescence spectrum between uncontaminated and contaminated corn fluorescence.

Step 207 detects aflatoxin contaminated corn pixels based on peak fluorescence and peak fluorescence shift features, where it is observed that healthy, uncontaminated target material has peak fluorescence features shifted toward shorter wavelength with higher peak fluorescence intensity, and aflatoxin contaminated corn has peak fluorescence features shifted toward longer wavelength with lower peak fluorescence intensity, in particular in the spectral range from 451 to 500 nm. Step 208 quantifies aflatoxin contamination levels within the imaged samples based on peak fluorescence, peak fluorescence shift features, and computed corn pixel statistics. Quantification is implemented through prediction models, such as regressions or neural network prediction, using spectrum values representing fluorescence intensity, mean, median, standard deviation, skewness, kurtosis, first order derivative, second order derivative, peak fluorescence location, peak fluorescence value, and normalized peak fluorescence difference index as independent variables, and aflatoxin concentration as dependent variable. Then, in step 116, as shown in FIG. 3, the analyzed fluorescence spectral imaging data regarding target material aflatoxin contamination detection and quantification output from the computer analysis system's processing is presenting in human-readable form.

FIG. 5a and FIG. 5b each show a top view of a portable fluorescence spectral imaging system in accordance with an alternative embodiment of the present invention. This portable fluorescence spectral imaging system is for the detection of aflatoxins in field conditions. The portable imaging system includes compartment 41, ultraviolet light source 42, preferably multiple rings of ultraviolet (UV) LED array, with the ultraviolet light source 42 inter-arranged with the spectral data acquisition device 43, preferably multiple rings of photodiode detector array. However, a micro-spectrometer array may also be used as spectral data acquisition device 43. The ultraviolet light source 42 is preferably centered at 365 nm and embedded with band pass excitation filter also centered at 365 nm. When a photodiode detector array is used as spectral data acquisition device 43, the photodiode detector array is embedded with an emission filter to block ultraviolet light with wavelength less than 400 nm from entering spectral data acquisition device 43. The photodiode detector array is also embedded with wavelength splitting optical instrument, such as narrow band pass filters in the wavelength range from 451 nm to 500 nm to capture peak fluorescence and peak fluorescence shift features of contaminated corn kernels. If a micro-spectrometer array is used as spectral data acquisition device 43, the micro-spectrometer array is embedded with an emission filter to only allow light of 400 nm and above to pass. To inspect target material 45, in this embodiment it is an ear of corn, it is first prepared or peeled and attached to inserter handle 46, as shown in FIG. 5*a*. Inserter handle 46 allows the user to insert the ear of corn into compartment 41 through the ultraviolet light source 42 (multiple rings of UV-LED array) and spectral data acquisition device 43 (multiple rings of photodiode detector array) and seal compartment 41 from outside light with inserter platform 44, as shown in FIG. 5*b*. Once inserter platform 44 fully closes compartment 41 inserter handle 46 is gradually pushed through the ultraviolet light source 42 (multiple rings of UV-LED array) and spectral data acquisition device 43 (multiple rings of photodiode detector array) for fluorescence spectral data acquisition. The collected spectral data are transferred to computer analysis system (not shown in FIG. 5*a* or 5*b*) for data analysis and generation of human-readable imaging information display (not shown in FIG. 5*a* or FIG. 5*b*).

Because of the portable nature of this embodiment a portable power source is provided (not shown in FIG. 5*a* or 5*b*). The portable power source is preferably a portable battery; however, other portable power sources may suffice. The computer analysis system and the portable power source, as appropriate, may be enclosed within compartment 41. The only portion of the portable fluorescence spectral imaging system of this embodiment that is not enclosed within compartment 41 is the human-readable imaging information display.

The foregoing disclosure, including the drawings, has been set forth merely to illustrate the invention and is not intended to be limiting. Since modifications, combinations and subcombinations of the disclosed embodiments incorporating the spirit and substance of the invention may occur to persons skilled in the art, the invention should be construed to include everything within the scope of the appended claims and equivalents thereof.

What is claimed is:

1. A method for aflatoxin detection using fluorescence spectral images, comprising the steps of: introducing target material before an ultraviolet light source; exciting the target material with ultraviolet light from the ultraviolet light source; passing fluorescence generated by the ultraviolet light excitation of the target material through a focusing device and a wavelength splitting optical device; detecting wavelength split fluorescence from the focusing device and the wavelength splitting optical device with a spectral data acquisition device which generates fluorescence spectral image data from the wavelength split fluorescence; transferring the fluorescence spectral image data from the spectral data acquisition device to a computer analysis system; processing the fluorescence spectral image data with the computer analysis system, wherein the processing includes pre-processing the fluorescence spectral image data with the computer system, identifying pixels associated with the target material in the fluorescence spectral images, computing statistics of spectral features for each identified target material pixel, characterizing fluorescence spectral features of each identified target material pixel, identifying peak fluorescence and peak fluorescence shift features within the characterized fluorescence spectral features, identifying aflatoxin contaminated target material pixels based on identified peak fluorescence and identified peak fluorescence shift features, and quantifying aflatoxin contamination levels within the imaged target material based on identified peak fluorescence and identified peak fluorescence shift features and computed target material pixel statistics; and presenting the analyzed fluorescence spectral imaging data regarding target material aflatoxin contamination detection and quantification results in human-readable form.

2. The method of claim 1, wherein
the target material is corn, and
the ultraviolet light wavelength is centered at approximately 365 nm.

3. The method of claim 2, wherein
the ultraviolet light source includes an ultraviolet lamp or ultraviolet light-emitting-diode array (UV-LED) and a band pass fluorescence excitation filter, and
the ultraviolet lamp or ultraviolet light-emitting-diode array and the band pass fluorescence excitation filter wavelengths are both centered at approximately 365 nm.

4. The method of claim 1, wherein the wavelength splitting optical device includes
a wavelength splitting optical instrument, and
a front-mounted long pass emission filter which blocks transmission of ultraviolet light with wavelength less than 400 nm.

5. The method of claim 4, wherein
the wavelength splitting optical instrument is one of a spectrograph, a set of separate filters having pre-defined wavelengths, or a tunable filter such as a liquid crystal tunable filter, an acoustic-optic tunable filter, or a filter wheel with a set of filters having pre-defined wavelengths.

6. The method of claim 1, wherein
the spectral data acquisition device includes an imaging camera or photodiode detector array, and
the imaging camera or photodiode detector array have an effective spectral response from 400 to 1000 nm.

7. The method of claim 1, wherein the pre-processing includes
dark current removal,
image calibration to convert from radiance values received at the spectral data acquisition device to fluorescence values of the target material,
spectral noise smoothing, and
noisy band removal.

8. The method of claim 1, wherein the spectral features are fluorescence spectrum values for each identified target material pixel.

9. The method of claim 2, wherein the characterizing fluorescence spectral features of each aflatoxin contaminated corn pixel is in the spectral range from 451 nm to 500 nm.

10. The method of claim 2, wherein the peak fluorescence and peak fluorescence shift features is in the spectral range from 451 nm to 500 nm.

11. The method of claim 2, wherein
aflatoxin contaminated corn kernel pixels are identified based on peak fluorescence and peak fluorescence shift features, where healthy, uncontaminated corn has fluorescence features shifted toward shorter wavelength and aflatoxin contaminated corn has fluorescence features shifted toward longer wavelength in the spectral range from 451 nm to 500 nm.

12. The method of claim 1, wherein
the quantification of aflatoxin contamination is further based on identified target material pixel statistics.

13. The method of claim 2, wherein the presenting step includes
presenting aflatoxin contaminated corn detection and quantification results including a corn sample grading report based on published aflatoxin regulations using different ppb (parts per billion) levels for differentiation, and aflatoxin contamination level for each corn sample.

14. A system for the detection of aflatoxin using fluorescence spectral imaging, comprising: at least one ultraviolet light source; at least one band pass excitation filter; a compartment for containing ultraviolet light generated by the at least one ultraviolet light source and excluding outside light, the at least one ultraviolet light source being located within the compartment such that light emitted from the at least one ultraviolet light source passes through the at least one band pass excitation filter and is incident upon target material which is introduced into the compartment; a spectral data acquisition device which detects fluorescence generated by excitation of the target material by the ultraviolet light and generates fluorescence spectral image data; at least one emission filter to block ultraviolet light with wavelength less than 400 nm from entering the spectral data acquisition device; at least one wavelength splitting optical instrument through which fluorescence generated by excitation of the target material by the ultraviolet light passes prior to entering the spectral data acquisition device; and a computer analysis system which receives and analyzes the fluorescence spectral image data generated by the spectral data acquisition device and presents at least a portion of the aflatoxin detection and quantification results of the analyzed fluorescence spectral image data in human-readable form, wherein the fluorescence spectral image data includes identified peak fluorescence and identified peak fluorescence shift features.

15. The system for the detection of aflatoxin using fluorescence spectral imaging of claim 14, wherein
the target material is corn;
the at least one ultraviolet light source wavelength is centered at approximately 365 nm;
the at least one band pass excitation filter is set at approximately 365 nm; and
the fluorescence spectral image data is in the spectral range from 451 nm to 500 nm.

16. The system for the detection of aflatoxin using fluorescence spectral imaging of claim 14, wherein the compartment includes
an aperture arranged to receive the fluorescence generated from the target material, and
a platform upon which the target material resides during excitation by the at least one ultraviolet light source.

17. The system for the detection of aflatoxin using fluorescence spectral imaging of claim 14, wherein
the platform is a conveyor which conveys the target material into and out of the compartment and into the field of view of the spectral data acquisition device.

18. The system for the detection of aflatoxin using fluorescence spectral imaging of claim 14, wherein
the platform is a tray that holds the target material in the field of view of the spectral data acquisition device.

19. The system for the detection of aflatoxin using fluorescence spectral imaging of claim 14, wherein
the spectral data acquisition device includes an imaging camera or photo-diode detector array.

20. The system for the detection of aflatoxin using fluorescence spectral imaging of claim 14, wherein
the at least one wavelength splitting optical instrument is one of a spectrograph, a set of separate filters having pre-defined wavelengths, or a tunable filter such as a liquid crystal tunable filter, an acoustic-optic tunable filter, or a filter wheel with a set of filters having pre-defined wavelengths.

21. The system for the detection of aflatoxin using fluorescence spectral imaging of claim 15, wherein
the at least one ultraviolet light source includes an ultraviolet lamp or ultraviolet light-emitting-diode array (UV-LED) and a band pass fluorescence excitation filter, and
the ultraviolet lamp or ultraviolet light-emitting-diode array and the band pass fluorescence excitation filter wavelengths are both centered at approximately 365 nm.

22. A portable system for the detection of aflatoxin using fluorescence spectral imaging, comprising: a portable power source; an ultraviolet light source; at least one band pass excitation filter; a compartment for containing ultraviolet light generated by the ultraviolet light source and excluding outside light, the ultraviolet light source being located within the compartment such that light emitted from the ultraviolet light source passes through the band pass excitation filter and is incident upon target material which is introduced into the compartment; a spectral data acquisition device includes a photo-diode detector array which detects fluorescence generated by excitation of the target material by the ultraviolet light and generates fluorescence spectral image data; an inserter for inserting the target material into and out the compartment and into the field of view of the spectral data acquisition device; at least one emission filter to block ultraviolet light with wavelength less than 400 nm from entering the spectral data acquisition device; a wavelength splitting optical instrument includes a set of separate filters having pre-defined wavelengths through which fluorescence generated by excitation of the target material by the ultraviolet light passes prior to entering the spectral data acquisition device; and a computer analysis system which receives and analyzes the fluorescence spectral image data generated by the spectral data acquisition device and presents at least a portion of the aflatoxin detection and quantification results of the analyzed fluorescence spectral image data in human-readable form, wherein the ultraviolet light source, the band pass excitation filter, the spectral data acquisition device, the at least one emission filter, and the wavelength splitting optical instrument are located within the compartment, and the fluorescence spectral image data includes identified peak fluorescence and identified peak fluorescence shift features.

23. The portable system for the detection of aflatoxin using fluorescence spectral imaging of claim 22, wherein
the target material is corn;
the ultraviolet light source wavelength is centered at approximately 365 nm;
the at least one band pass excitation filter is set at approximately 365 nm; and
the fluorescence spectral image data is in the spectral range from 451 nm to 500 nm.

24. The portable system for the detection of aflatoxin using fluorescence spectral imaging claim 22, wherein the inserter includes
- an inserter handle arranged to support the target material; and
- an inserter platform arranged to act as a seal to contain the ultraviolet light and exclude outside light from entering the compartment when the inserter is fully inserted into the compartment.

25. The portable system for the detection of aflatoxin using fluorescence spectral imaging of claim 22, wherein
the inserter is a tray that holds the target material in the field of view of the spectral data acquisition system.

26. The portable system for the detection of aflatoxin using fluorescence spectral imaging of claim 22, wherein
the spectral data acquisition device includes a photodiode detector array or a micro-spectrometer.

27. The portable system for the detection of aflatoxin using fluorescence spectral imaging of claim 23, wherein
- the ultraviolet light source includes an ultraviolet light-emitting-diode array (UV-LED) and a band pass fluorescence excitation filter, and
- the ultraviolet light-emitting-diode array and the band pass fluorescence excitation filter are both centered at approximately 365 nm.

* * * * *